United States Patent [19]

Pinkowski

[11] Patent Number: 5,395,493
[45] Date of Patent: Mar. 7, 1995

[54] METHOD FOR DETERMINATION OF PERACIDS

[75] Inventor: Alexander Pinkowski, Rothenberg, Germany

[73] Assignee: ProMinent Dosiertechnik GmbH, Heidelberg, Germany

[21] Appl. No.: 91,896

[22] Filed: Jul. 14, 1993

[30] Foreign Application Priority Data

Jul. 15, 1992 [DE] Germany .................. 42 23 228.7

[51] Int. Cl.6 .................................. G01N 27/26
[52] U.S. Cl. .................. 204/153.1; 204/153.2; 204/412; 204/434
[58] Field of Search .................. 204/153.1, 153.2, 400, 204/434

[56] References Cited

U.S. PATENT DOCUMENTS

| | | | |
|---|---|---|---|
| 3,644,824 | 2/1972 | Barker et al. | 324/31 |
| 4,947,153 | 8/1990 | Berger | 340/608 |
| 4,988,418 | 1/1991 | Beck et al. | 204/434 |
| 5,214,964 | 6/1993 | Hartfiel | 73/861 |

FOREIGN PATENT DOCUMENTS

| | | |
|---|---|---|
| 0322631B1 | 12/1988 | European Pat. Off. . |
| 0333246A2 | 3/1989 | European Pat. Off. . |
| 3136248A1 | 9/1981 | Germany . |

OTHER PUBLICATIONS

*Electro-Chemical Kinetics*, by Dr. Klaus J. Vetter, Springer-Verlag 1961, pp. 68–81.
Kolthoff et al., *Polarography*, 2d. rev. ed., vol. II, (1952)*, p. 573–574.

Primary Examiner—T. Tung
Attorney, Agent, or Firm—Darby & Darby

[57] ABSTRACT

A method is described for definition of peracids in the presence of hydrogen-peroxide in a solution with the following steps:

(1) introducing an electrode-design, which provides at least one measurement electrode and one counter electrode into the solution, (2) Loading of the electrodes with varying potentials; and (3) Measurement of the current by using a measurement electrode.

With such a method the peracid solutions always contain hydrogen-peroxide, which also shows similar reactions.

In order to determine the peracid concentration, a value of the determined current is compared with a corresponding value of an earlier recorded electrode-design.

26 Claims, 2 Drawing Sheets

METHOD FOR DETERMINATION OF PERACIDS

FIELD OF THE INVENTION

The invention under consideration, is a method wherein the determination of peracids with hydrogen-peroxide present can be solved with the following steps:
  Introduction of an electrode-design, which provide at least one electrode for measurement and one counter electrode in the solution,
  Loading of the electrodes with varying potentials and
  Measuring the current through the measurement electrodes.

BACKGROUND OF THE INVENTION

Peracids, especially per-acetic acid, due to their bactericidal, fungicidal, sporicidal and virucidal effects with environmental reaction products (e.g. per-acetic acid: acetic acid, hydrogen and oxygen ) are often brought into action as disinfectants. Per-acetic acid, particularly, especially in diluted solutions with high temperatures and pH-values decomposes in time. Thus, for the use of peracid containing solutions it becomes necessary to determine the per-acid content with regularity to assure the desired effect.

The quantitative determination of peracid is difficult, because watery peracid solutions always contain hydrogen-peroxide, which shows similar reactions. With titimetric determinations two different reagents are consecutively employed in order to determine quantitatively the contents or the concentration of peracid, e.g. per-acetic acid and hydrogen-peroxide next to each other. EP 0 322 631 B1 offers a method and reaction for the determination of per-acids next to hydrogen-peroxide, whereby a sampling is required. After the mixing of a test solution with the proper reaction-solution in a cuvette, a certain reaction-time will determine the extinction by using a spectro-photometer. The data will be compared with a calibration curve.

This known method requires much time, proper equipment and trained personnel.

BACKGROUND OF THE PRIOR ART

A method mentioned in the beginning is known from EP 0333 246 A2. In this case an ampere-meter test is carried out, whereby the used potential difference is not visible. Measurements of this kind are usually carried out in Faraday's range, in which surface-film currents which in essence mirror the synthesis as well as the decomposition of surface-films (e.g. hydrogen- and oxygen-chemical sorption layers) superimpose the current-voltage characteristics of the corresponding electrode-reaction of the to be tested materials. The magnitude of these currents depends on the concentration of the to be tested materials. In order to eliminate the influences and the breakdowns through hydrogen-peroxide during tests of peracids if possible, it is proposed in a known case, to use a porous isolator which covers the measurement electrode and separates it from the testing-liquid and will greatly eliminate the influences of the hydrogen-peroxide.

SUMMARY OF THE INVENTION

The submitted invention has basically the purpose to provide a method for determination of peracids which can easily be automated to indicate the presence of hydrogen-peroxide and also allows a relatively accurate determination of the peracid concentration.

This task will be resolved by using a method, initially mentioned, through which the potential difference in the range of the double layer is selected and a peracid-concentration will be determined by comparing the indicated value of the current with a corresponding assigned value for the electrode-design, recorded at an earlier calibration function.

DETAILED DESCRIPTION OF THE INVENTION

Figure 1:
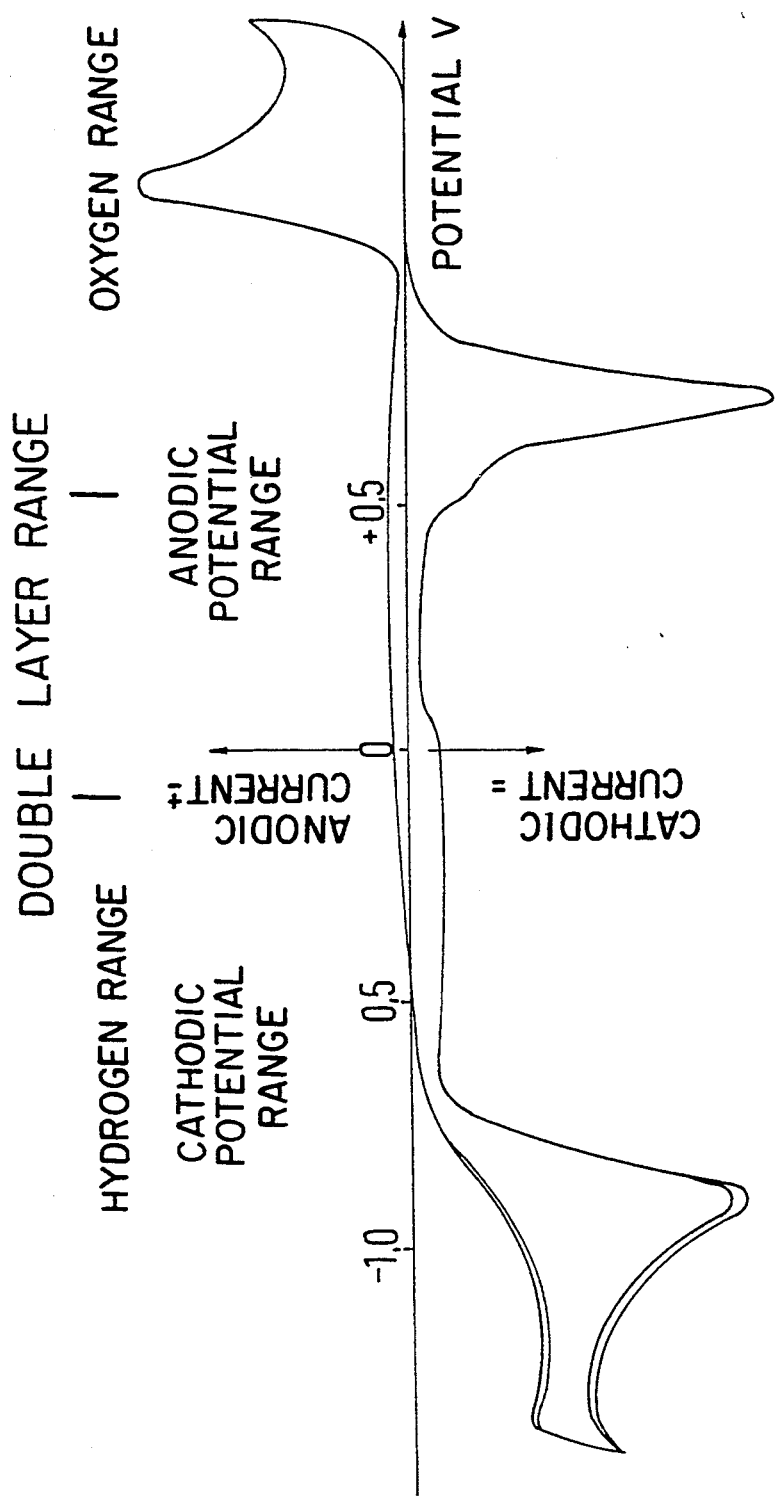

The double layer range is a voltage- or potential-difference range, wherein the measurement electrode forms an electro-chemical or electrical double layer. This acts like a condenser with an extremely small plate-distance. Up to now the assumption has been that a current with a voltage- or potential difference, which flows from the double layer range, is merely an unloading current, by which this condenser will be reloaded. In the double layer range normally no Faraday's reaction take place (e.g. a reduction or oxidation of an electro-chemically active specimen, such as hydrogen-peroxide or peracid). In the double layer range there could be preliminary steps to form the surface-layer connections. It was surprising to learn that the components of this very small current show a dependence to the peracid concentration relative to the Faraday's currents in the solution which surrounds the measurement electrode. Although the regularity of this occurrence has not been fully understood, one could assume that the preliminary stages of the surface layer connections have already been catalytically active and the desired electro-chemical reduction of the peracid terminates almost without any influence of the hydrogen-peroxide present. There are two more effects complementing each other for the determination of the peracid. For one, a peracidal-specific reaction can take place. Concerning the other, if the polarization effects do not take place here. They might possibly prevent an advance of the peracid in Faraday's range toward the measurement electrode. The preliminary steps of the surface layer connections with their catalytic effect cover the surface of the measurement electrode to an almost nonexisting extent, e.g. a fraction of one percent. They are, however, sufficient to produce a peracid-specific current. Remedial measures, such as porous isolators are unnecessary. The comparison with a prior calibration function makes the evaluation possible, without the need to know the basic regulations. The calibration function does not need to conform to the same, but can also be done with an equivalent electrode-design. The calibration function can be illustrated, for instance, in the form of a calibration curve, or in the form of a matrix, a table or any other kind of value presentation.

Preferably a potential-difference will be selected to be in the range at the middle third of the double layer range. It was found that in this range the least breakdowns due to hydrogen-peroxide occur. A much better approach to optimal test results can be achieved by an electrode-design, whereby the first voltage-cycle is loaded within the double layer range and the maximum of the current is determined. The maximum of the current can be compared with the calibration function. A voltage cycle is understood to mean a chronologically variable voltage which, within a pre-determined period changes at least once in a positive and at least once in a negative direction, whereby the starting and the finish values basically agree with each other. In this case, one no longer depends on showing the correct potential-difference at the first try. One can approach the optimal voltage value iteratively. With maximum current, disturbing influences of hydrogen-peroxide can be neglected for all practical purposes.

Preferably, the calibration function will bring forward in the electrode-design a series of solutions known to produce varying peracid concentrations, whereby for each concentration passing through the first voltage cycle the maximum current is determined. The individual solutions with varying concentrations will, for instance, be produced from a stock solution with increasing dilution. The values between the known concentrations at the determination or measurement of peracid can, if necessary, be established by interpolation.

As is preferred, the electrode arrangement can be brought into a solution free of peracid and the voltage cycle will be run through. In doing so, the value of the unloading current of the electro-chemical double layer can be determined and then computed. As an advantage an electrode-design is loaded with a second voltage cycle. With a symmetrical voltage variation, particularly on both sides of the zero-line, the maximum values are limited by the potential ranges of the electrolytic disintegration of the solution. It does not absolutely have to reach these potential ranges. The use of this second voltage cycle regenerates the measurement electrode. Products of oxidation and reduction, which in spite of everything, attach themselves to the measurement electrode, can be removed. Aging influences of the electrode are thereby substantially eliminated.

It is preferred when running through a voltage-cycle of the measurement electrode, that an electro-catalytically active layer is produced and it completely disintegrates. The total disintegration of the catalytic layer at each voltage-cycle assures the creation of a fresh surface of the measurement electrode for the succeeding measurement. Symptoms of aging are thereby prevented. In this way, accurate and reproducible measurement results can be achieved. However this demand sets a limit with respect to the speed the voltage cycle, can run through. Within the voltage cycle sufficient time is needed for the electro-chemical reaction of the electrode with the solution to run to its completion. Time is also required for the fresh production of the catalytic layer and its total synthesis. Furthermore, the voltage cycle must show a certain minimal voltage as an extreme value.

It is also a preference to run through several second voltage cycles before the measurement, long enough that either a certain number of second voltage cycles are reached, or the current-runs of successive voltage cycles do not vary more than a certain pre-determined measurement. The actual measurement starts only when, after the run of the second voltage cycles, a stable condition exists or can be expected. Generally it suffices to have an activity time of approximately 10 minutes with a potential speed change of approximately 100 mV per second and approximately 8 to 12 voltage cycles. This will largely eliminate aging influences of the electrodes.

At least two measurement electrodes are used advantageously. One of them, while running a voltage cycle in a basically peracid concentration, and the other produces a basically proportional current-signal to the hydrogen-peroxide concentration. This signal is used for the fine-adjustment of the peracid concentration-current signal. Such a method is particularly advantageous when a large surplus of hydrogen-peroxide exists, e.g., a tenfold surplus. If the measurement electrodes are used in proper sequence, the mutual influence will not occur.

It is also preferred within the first voltage cycle of the potential ranges where no maximum current can be expected, to run through much faster. The method has the advantage that for the measurement of the current and the evaluation of the maximum, more time is available without prolonging the cycle essentially. The evaluation will be particularly simplified, when, during the first voltage cycle, the potential is kept constant at a designated value during a designated time. If it is advantageous the values are the potential-value with the desired maximum current or a closely neighboring value. One can for the evaluation use relatively simple and therefore inexpensive methods and devices.

Instead of using a voltage cycle, one can do the determination by loading the electrodes in sequence and by varying the voltage blocks, which are basically rectangular. Such a technique can also be called "the potential-jump technique". Instead of fully running through a voltage cycle, one jump-starts for a relatively short time only a few, particularly three, characteristic potentials respectively potential-differences. These potentials,the proper holding times and the duration of the voltage blocks are chosen to have the same kind of activation of the work-electrode or the measurement as with cyclovoltametry. This means measurement with the use of one or several voltage cycles.

It is preferred that the voltage blocks have varying potential differences and at least one (but particularly all) shows different lengths. One has herewith two sources of influence available to effect a desired control of the electrodes. These are namely the amplitude and the length of the blocks. In this way the method can be adapted in the wider ranges of selected species.

It is also advantageous that the potential differences of the various voltage blocks are so developed that a first one is an anodal oxidation potential, a second one is a reduction potential and a third one is a measurement potential. Basically the potentials should be designated as the "potential differences". The term "potential" is maintained, because of its shortness. One assumes that with an anodal oxidation potential of the work electrode the creation of preliminary steps of a surface-oxide occurs. These are effective for the analysis of peracid catalytically. With the reduction potential, the reduction of the oxide takes place. With the measurement potential, the electro-chemical reduction for the measurement with the peracid is required. With this, one can get the same effect as with the voltage cycle by using equipment for three suitable potential differences.

It is an advantage when the measurement potential, and especially also the reduction potential are arranged to be in the middle of the double layer range. As demonstrated above, outside the Faraday's range there is an established measurement value, which is basically proportional to the peracid concentration, although we would not have expected corresponding currents here.

Preferably, the length of the voltage block with the measurement potential is substantially larger than the mass of the other voltage blocks. For the measurement a sufficient amount of time is available. The other voltage blocks serve simply for the measurement preparations and can therefore be much shorter.

As an advantage, three voltage blocks together have a duration of less than 10 seconds. One can within one cycle of a few seconds perform the required measurement by switching three suitable potentials. This permits short reaction times with accurate measurements.

As an advantage the counter electrode in the solution is not polarizable. This can, for instance, be achieved by having the surface of the counter electrode, which is in contact with the solution, be substantially (e.g. a hundred times) larger than the contact surface of the measurement electrode. With such a configuration one can manage with two electrodes. The counter- or auxiliary-electrode takes over the function of the reference-electrode.

One can use a reference-electrode in addition, in order to adjust the potential of the measurement electrode exactly. This can be achieved with the aid of potential-static switching. In this case one needs for the evaluation of the current-signal not only the voltage between measurement- and counter-electrode, but also the potential of the individual electrodes, which if necessary will obtain more accurate measurements.

For the fastening of the potential of the reference-electrode it is preferable to use a polymer-electrolyte, which is built up as a particular internal electrolyte. This polymer-electrolyte endures both very high temperatures (ca. 100° C.) and measures a measurement solution, which was soiled by electrode-poisons, such as sulfides and similar chemicals.

The preference for use as a measurement electrode is a membrane-covered electrode. The use of a membrane-covered electrode substantially reduces the dependence of the measurement-signal from the flow-velocity of the measurement electrode through the solution, and the danger to soil of the measurement electrode as well. The result is an equalization of the measurement-signal.

The preference is to use at least one micro electrode as a measurement electrode. The micro electrodes are electrodes, because the linear expansion of their contact surfaces with the solution is smaller than the thickness of the diffusion layer. The thickness of the diffusion layer will be determined by the concentration of the ions of the measurement solution and generally are a few micro-meters. A typical linear expansion of a micro electrode amounts to less than 10 $\mu$m. The use of micro electrodes make it possible to take measurements in poor conducting medias, even when a sufficient oncoming flow of the measurement electrode is absent. A membrane can also be canceled.

A measurement electrode can also be used as an open macro electrode in a flow element, which is exposed to a defined oncoming flow. With macro electrodes the linear expansion of their contact surface with the solution is larger than the thickness of the diffusion layer. Especially with a potentio-dynamic method of operation it appears that in the case of a diffusion-limited reaction at the macro electrode the maximum current at the run of the first voltage cycle can be used for the evaluation of the concentration of the peracid.

In order to examine solutions with extreme pH-values, e.g. pH<1, or in an extreme temperature-range, e.g. >80° C., current element can be tempered and/or be provided with a buffer solution. In doing so, better working conditions for the method of measurement will be established.

A preferred given range for the measurement is at room temperature, which is at about 20° to about 30° C., if the solution is weakly sour or neutral (pH5-7).

The method becomes particularly simple when the calibration function is recorded in a data-logger. It should be applied during or before the use of the electrode-design design in a signal-processor to evaluate the current-signals. The data-logger will be displaced together with the electrode-design. For each electrode-design a data-logger is required, which contains the typical values for the electrode-design. The signal processor can be designed equally for all electrode-designs. It only records specific values for each present electrode-design.

The invention is described with the following available examples.

The drawings show in

Figure 2:
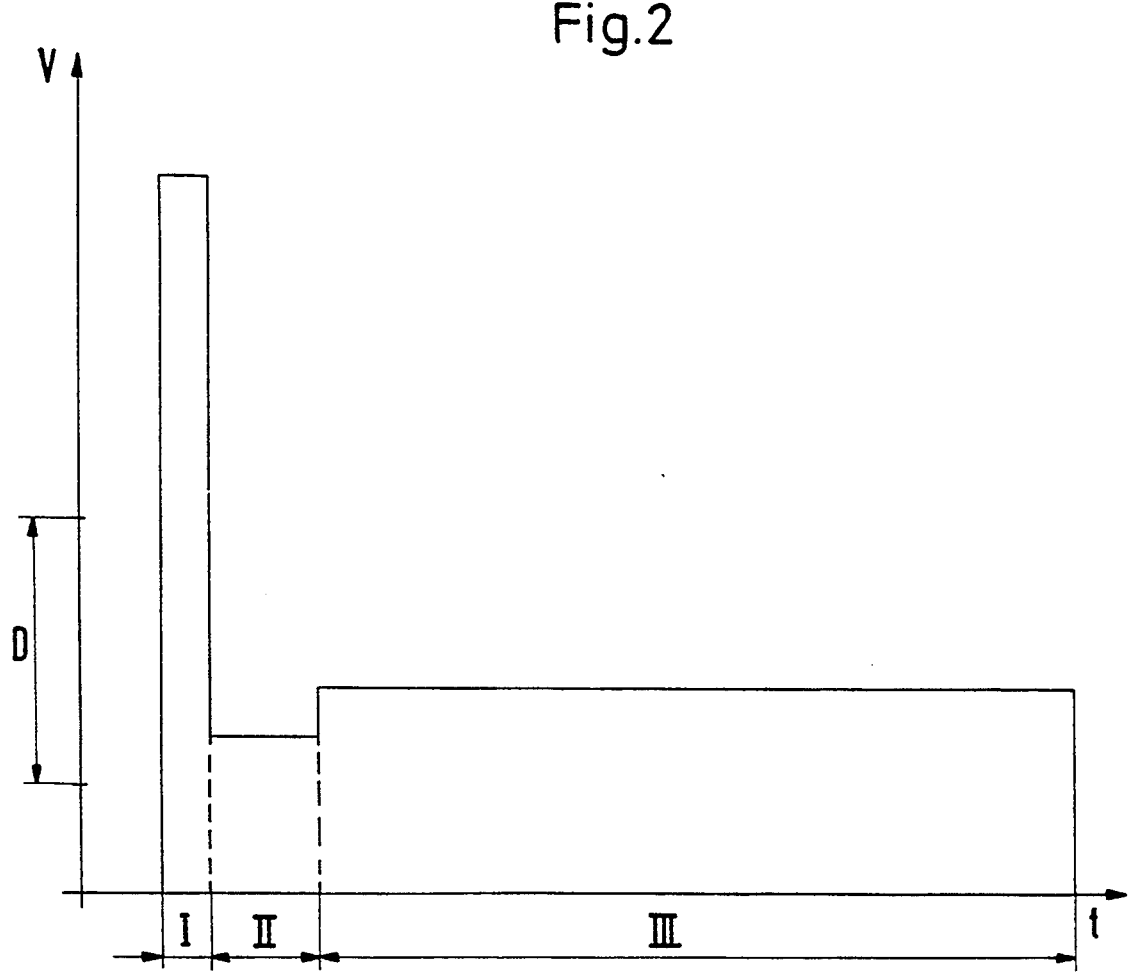

FIG. 1 a cycle-voltagram of a peracid-free solution;

FIG. 2 the application of a potential jump-technique, which serves to demonstrate the concepts. The curve was recorded by the use of a gold operation electrode, a platinum counter electrode and a silver/silver-chloride reference-electrode (3 m KCl) at room-temperature without any nitrogen-circulation. The speed was 100 mV/s, while the potential is given visa vis the reference-electrode.

EXAMPLE 1

Determination of peracids by using a gold- measurement electrode, determination of a calibration function A usual three electrode arrangement is used, consisting of a measurement or operation-electrode, a reference electrode and an auxiliary-or counter-electrode. A gold wire of clearness m3N, a diameter of 1 mm and a length of 5 mm (Johnson Matthay Alfa Products 00727) will be cast to half of its length in epoxy-resin (Araldit Ciba Geigy 2545), ground and polished. This gold wire serves as a measurement electrode and the two other electrodes are a commercial silver-silverchloride-electrode (Schott B 3420) as a reference-electrode and a super-refined steel plate (e.g. Werkstoff 1.4571) with a 1 $cm^2$ surface as an auxiliary electrode. The measurement electrode and the auxiliary electrode will be treated for 5 minutes in an ultrasonics bath in a usual cleaning solution (e.g. 10% RBS 50-solution by the Firm C.Roth), in order to make the surfaces fat-free. The reference- electrode will be applied without any prior treatment. All measurements are carried out at room temperature.

For the determination of the peracid-free base-curve the three named electrodes will be dipped in solution 1 (ground-electrolyte) in a conventional analyzer with a cover and a possibility of a gas-installation. It will be connected with the provided terminals to a potentiostat (PAR 273 by EG&G). The solution 1 will be measured twice. Once, it will be used as applied, meaning air-saturated and the other time it will be made almost oxygen-free by a 30-minute introduction of nitrogen before the measurement.

Solution 1:

71.02 g Sodium-sulfate (Merck 6649) will be dissolved in 0.5 distilled water and will be adjusted by adding of 0.1 normal salt-acid to a pH-value of 4.0.

With the aid of a potentiostat and one X-Y-writer connected to it (e.g. Rikadenki model RW-201T), a cyclic current-voltage-curve (cyclovoltamogram) will record the electrolytic disintegration of the measurement-solution through hydrogen- and oxygen-development within the potential-ranges in a conventional way. In this case the ranges are $-1.4$ V (cathodic reversal potential) and $+1.5$ V (anodic reversal potential). All potential data, when expanded, refer to the potential of the operating electrode in contrast to the silver-/silver-chloride-reference electrode. The stationary final condition of the cyclovoltamogram is reached after 10 completed runs between cathodic and anodic reversal potential. This means the ninth and tenth run are hardly different. 100 mV/s were chosen as the potential feeding speed. The cyclovoltamogram, which was recorded in an air-saturated base-electrolyte, is later used as a zero-curve to correct the cyclovoltamogram recorded in peracid containing solutions. From the cyclovoltamogram in the oxygen-free base-electrolyte the double layer range is determined. It lies in the demonstrated case between −100 and +500 mV.

After the recording of the cyclovoltamogram in the base-electrolyte the measurement vessel will be cleaned with distilled water and filled with solution 2.

Solution 2:

71.02 g sodium-sulfate (Merck 6649) will be dissolved in 0.5 L distilled water. Then 3mL 32% peracetic acid-solution (Aldrich 26,936-6) are added and is adjusted to a pH-value of 4.0 as in solution 1.

The described solution 2 contains approximately 200 mg peracetic acid per liter of solution (2000 ppm). Peracetic acid always disintegrates up to a certain percentage into hydrogen-peroxide and acetic acid. The exact peracetic acid containment of solution 2 can be determined in a titrimetic and conventional way by using potassium-iodine, sulfur acid, sodium-thiosulfate and potassium permanganate. By using the given stabilized peracetic acid by Aldrich the hydrogen-peroxide portion amounts to less than 6%.

Solution 2 serves as stock solution for the manufacture of peracetic acid solution with reduced peracetic acid content. This is done by mixing of solution 2 with solution 1. In order to obtain a peracetic acid solution, for instance, which contains only one tenth of the peracetic acid content of solution 2, 50 mL of solution 2 will be mixed with 450 mL of solution 1. In this way solutions with 1000, 500, 200, 100, 50, 20, 10, 5 and 2 ppm of the peracetic acid are produced.

Titrated solution 2 was manufactured in this fashion and also the weaker concentrated peracetic acid solutions were produced by dilution in a similar way. As described above for ground-electrolytes, cyclovoltamograms in the potential range −1.3 V and +1.5 V are also recorded at first. Afterwards further cyclo- voltamograms in the double layer range, are recorded. Finally from this cyclovoltamogram in the double layer range the potential range is determined. In this potential range in which a cathodic maximum of the current measurement signal appears, it is proportional to the peracetic acid content of the solutions. In this potential range the cyclovoltamogram with much reduced potential feeding speed (2 mV/s) is run through. The determined values of the current maximum of the air-saturated ground electrolytes with equal potential determined current values are deducted.

In this way 10 corrected pairs of values of peracetic acid concentration and current signals are determined, which when applied graphically result in a linear calibration-curve. We can gather from this that the applied sensor arrangement can be used at least in the range of 2-2000 ppm peracetic acid. The sensitivity of the sensor arrangement (incline in the calibration-curve) amounts with the given temperature and pH-conditions to 0.15 nA/ppm peracetic acid.

Example 2

Determination of the influence of a surplus of hydrogen-peroxide on the peracetic acid-signal.

There is an equal measurement arrangement as in example 1 applied (three-electrode measurement analyzer, potentiostat, writer, cyclovoltamogram). At this time the stock solution will produce three measurement solutions with constant peracetic acid concentration with, however, increasing quantities of hydrogen-peroxide.

Solution 3:

71.02 g Sodium-sulfate (Merck 6649) and 0.6 mL 32% peracetic acid (Aldrich 26,936-6) will be dissolved in 0.5 L water and a pH-value of the solution as in example 1 adjusted to 4.0. This stock solution 3 contains approx 400 ppm peracetic acid and 25 ppm hydrogen-peroxide. The exact contents will be determined by titration as in example 1.

From solution 3, by adding 30% of hydrogen-peroxide solution (Merck7209), measurement solutions with higher hydrogen-peroxide content are produced. The concentration proportion of peracetic acid to hydrogen-peroxide is varied in this way from 1:1 to 1:20.

In the same way as in example 1, cyclovoltamograms in the entire potential range, namely from −1.3 to +1.5 V in the measurement solutions with increasing hydrogen-peroxide surplus, are recorded and are corrected with respect to ground-electrolyte current.

It can be established that by running through the cyclovoltamogram of anodic to cathodic direction (cathodic from a relatively small, cathodic peracetic acid-current maximum signal I), and outside the double layer range, there occurs a further large, narrow cathodic current maximum (signal II). The height and width of this current maximum grows with increasing surplus of hydrogen-peroxide, which can be associated with the cathodic reduction of this substance. With signal II it involves a typical Faraday's reaction in the range of the hydrogen in the cyclovoltamogram. Additional cathodic influence in the range of the hydrogen causes a further high, wide, cathodic current maximum (signal III), whose signal height increases with growing peracetic acid concentration and also with growing hydrogen-peroxide concentration. Signal III is because of this double dependence (transverse strain sensitivity vis-a vis hydrogen-peroxide) not suited for the peracid-determination.

Now, when one records cyclovoltamograms in the same solutions with increasing hydrogen-peroxide surplus in the double layer range, one finds out that signal I, with increasing hydrogen-peroxide surplus changes at first its shape and then becomes a current plateau. Finally, it shows only a shoulder which clearly lies outside the double layer range of a much larger current signal. From the knowledge gained through the cyclovoltamogram in the entire potential range, one can see that this disturbing current-signal is the signal II.

With the determined data one is in a position to estimate the hydrogen-peroxide surplus, signal I deviates less than a pre-determined tolerance of pure peracetic acid signal without hydrogen-peroxide surplus. In the result of this evaluation one finds that with up to 15-times surplus of hydrogen-peroxide, the adulteration of signal I amounts to less than 10%.

The same results can also be achieved by potential-jump-technique. As shown in FIG. 2, it is not necessary to run through a complete voltage-cycle. One is more concerned with an electrode design and three voltage blocks in sequence, designated in FIG. 2 as I, II, and III. As can be seen, the three voltage blocks have not only varying amplitudes, but also differing lengths. In voltage block I, a so called anodic oxidation potential is applied, which presumably forms on the operating electrode the preliminary steps of a surface-oxide. They are catalytically effective for the peracid-evidence.

In voltage block II, a so called reduction potential is applied, which causes the reduction of this oxide. In voltage block III a measurement potential is applied with which the electro-chemical reduction of the peracid takes place, which is required for the measurement. The reduction potential in voltage block II, as well as the measurement potential III are located in the middle of the double layer range D. The voltage block III has the largest length, which means it is substantially larger than the voltage blocks II and I.

What is claimed is:

1. A method for the determination of a peracid in a solution in the presence of hydrogen-peroxide comprising the following steps:
   a. introducing at least two electrodes, including a measurement electrode and a counter electrode, into the solution;
   b. varying a potential difference between the measurement electrode and the counter electrode if no separate reference electrode is also employed, or between the measurement electrode and a reference electrode if a separate reference electrode is also employed; and
   c. measuring a current using said measurement electrode at a potential difference that is selected in a double layer range, and determining the concentration of the peracid by comparison of the measured current with a calibrated value.

2. The method of claim 1, wherein the potential difference is selected to be in the range of the middle thirds of the double layer range.

3. The method of claim 1, wherein a first voltage cycle is applied within the double layer range and wherein a maximum current value is determined and compared with a maximum current of a calibration cycle.

4. The method of claim 3, wherein the calibration cycle is produced by placing said measurement electrode and counter electrode in a series of solutions with known varying peracid concentrations, whereby for each concentration the first voltage cycle is run through and the maximum current is determined.

5. The method of claim 3, wherein the measurement electrode and counter electrode are also introduced into a peracid-free solution and a first voltage cycle is run through.

6. The method of claim 3, wherein before measurement, several second voltage cycles are run through until either a predetermined number of second voltage cycles is reached or the current variations of consecutive voltage cycles do not vary more than a pre-determined amount.

7. The method of claim 3, wherein potential ranges within the first voltage cycle in which no current maximum is to be expected are run through faster than potential ranges within the voltage cycle where a current maximum is expected.

8. The method of claim 7, wherein within the first voltage cycle the potentials are kept constant at a pre-determined value for a pre-determined period of time.

9. The method of claim 1, wherein a second voltage cycle which has a symmetrical voltage variation on both sides of the zero-line, maximum values being limited by potential ranges of electrolytic disintegration of the solution, is applied to the measurement electrode and counter electrode.

10. The method of claim 9, wherein as a result of the second voltage cycle, an electro-catalytically active layer is produced on the measurement electrode and becomes fully disintegrated.

11. The method of claim 1, wherein at least two measurement electrodes are used through a voltage cycle, one essentially in peracid concentration and the other producing current-signals proportional to the hydrogen-peroxide concentration, for fine-tuning the measured current.

12. The method of claim 1, wherein different, basically rectangular voltage blocks are applied to the electrodes.

13. The method of claim 12, wherein at least one voltage block has a length varying from the others.

14. The method of claim 12, wherein from potential differences of the voltage blocks, a first voltage block is designed as an anodic oxidation potential, a second voltage block is designed as a reduction potential, and a third as a measurement potential.

15. The method of claim 14, wherein the measurement potential is in the double layer range.

16. The method of claim 14, wherein the reference electrode uses a polymer-electrolyte.

17. The method of claim 12, wherein the length of a voltage block with measurement potential is substantially larger than the length of all other voltage blocks.

18. The method of claim 12, wherein three voltage blocks together show a length of less than 10 seconds.

19. The method of claim 1, wherein the counter electrode cannot be polarized in the solution.

20. The method of claim 1, wherein a separate reference electrode is used.

21. The method of claim 1, wherein a membrane-covered electrode is used as a measurement electrode.

22. The method of claim 1, wherein the measurement electrode comprises at least one micro-electrode.

23. The method of claim 1, wherein an open macro-electrode is used as a measurement electrode in a flow-element which is exposed to a defined flow.

24. The method of claim 23,, wherein the flow-element is provided with buffer solution.

25. The method of claim 1, wherein the measuring is done in a weak acid or neutral solution at room temperature.

26. The method of claim 1, wherein the calibrated value is determined in a data-logger, which before or during the method is recorded in a signal-processor.

* * * * *